(12) United States Patent
Cook et al.

(10) Patent No.: US 6,984,602 B2
(45) Date of Patent: Jan. 10, 2006

(54) OLEFIN POLYMERIZATION CATALYSTS CONTAINING A PYRROLE BISIMINE LIGAND

(75) Inventors: Jessica Cook, Clinton, NJ (US); Inna Shulman, Dayton, NJ (US); John Joseph Bielak, South Amboy, NJ (US)

(73) Assignee: Univation Technologies, LLC, Houston, TX (US)

( * ) Notice: Subject to any disclaimer, the term of this patent is extended or adjusted under 35 U.S.C. 154(b) by 49 days.

(21) Appl. No.: 10/477,560

(22) PCT Filed: Apr. 25, 2002

(86) PCT No.: PCT/US02/14973

§ 371 (c)(1),
(2), (4) Date: Sep. 2, 2004

(87) PCT Pub. No.: WO02/090366

PCT Pub. Date: Nov. 14, 2002

(65) Prior Publication Data

US 2005/0014634 A1 Jan. 20, 2005

Related U.S. Application Data

(60) Provisional application No. 60/352,469, filed on Jan. 28, 2002.

(51) Int. Cl.
*B01J 31/00* (2006.01)
(52) U.S. Cl. ............... 502/150; 502/155; 502/162; 502/167; 548/402; 556/13; 534/15; 534/11
(58) Field of Classification Search ............... 502/150, 502/155, 162, 167; 548/402; 556/13; 534/15, 534/11
See application file for complete search history.

(56) References Cited

U.S. PATENT DOCUMENTS

| 6,184,171 B1 * | 2/2001 | Shih ............... 502/158 |
| 6,294,495 B1 * | 9/2001 | Matsunaga ............ 502/103 |
| 6,300,439 B1 * | 10/2001 | McConville ............ 526/161 |
| 6,686,306 B2 * | 2/2004 | Shih ............... 502/113 |
| 6,800,766 B2 * | 10/2004 | Jacobsen et al. ........ 549/230 |

FOREIGN PATENT DOCUMENTS

| EP | 0924223 A | 6/1999 |
| JP | 2001 261638 | 9/2001 |
| WO | WO 98/27124 | 6/1998 |
| WO | WO 98/30612 | 7/1998 |
| WO | WO 98/46651 | 10/1998 |
| WO | WO 99/02472 | 1/1999 |
| WO | WO 99/12981 | 3/1999 |
| WO | WO 00/69923 | 11/2000 |

OTHER PUBLICATIONS

Dawson et al., 'Synthesis and reactivity of sterically hindered iminopyrrolato complexes of zirconium, iron, cobalt and nickel', J. Chem. Soc., Dalton Trans., 2000, 459-466.*
Fryzuk, "*The 1992 Alcon Award Lecture Excursions around the periodic table ligand design in inorganic chemistry*" Can. J. Chem., vol. 70, p. 2839 (1992).
Bochmann et al., "*Synthesis and reactivity of sterically hindered iminopyrrolato complexes of zirconium, iron, cobalt and nickel*" J. Chem. Soc., Dalton Trans., 459 (2000).
Edwards, et al., "*New Dialkylamido Complexes of Transition Metals in Group 4 and 5 stabilised by Terdentate Ligands*" J. Chem. Soc., Dalton Trans., p. 1253 (1989).
van Koten, et al., "*Intramolecularly Chelated Di- and Tetranuclear Aryllithium Compounds: Crystal Structure of $Li_4[C_6H_4(2-CH_2NMe_2)]_4$ Containing Four-Center Two-Electron Bonded C(aryl)Atoms and Heptacoordinate Lithium Atoms*" J. Am. Chem. Soc., vol. 104, p. 5490 (1982).
Wayland, et al. "*Pyrrole Diimine Copper Complexes for Initiation and Control of Atomtransfer Radical Addition and Polymerization Processes*" Polymer Preprints, American Chemical Society, US. vol. 41, No. 2, p. 307-308 (1999).
Matsuo, et al., "*Selective Formation of Hompleptic 2,5-Bis (N-aryliminoethyle)pyrroly Yttrium Complexes and Their Performance as Initiators of c-Caprolactone Polymerization*" ORGANOMETALLICS, 20, 3510-3518 (2001).

* cited by examiner

*Primary Examiner*—J. A. Lorengo
*Assistant Examiner*—Jennine Brown

(57) ABSTRACT

Polydentate substituted pyrrole based chelants, metal complexes containing the same, olefin polymerization catalyst compositions, and polymerization processes using the same.

8 Claims, No Drawings

OLEFIN POLYMERIZATION CATALYSTS CONTAINING A PYRROLE BISIMINE LIGAND

CROSS-REFERENCE TO RELATED APPLICATION

This present application claims priority to U.S. Provisional Patent Application Ser. No. 60/352,469 filed Jan. 28, 2002.

The present invention relates to transition metal compositions useful as components of catalyst compositions for olefin polymerization. More particularly, the present invention relates to a transition metal complex incorporating a polydentate, pyrrole containing ligand group.

The use of Group 3–10 metal complexes as a component of a catalyst composition used in the polymerization of olefins is well-known. Metallocenes are organometallic coordination complexes containing a metal in association with one or more π-bound ligands, typically cyclopentadienyl groups of substituted derivative thereof. Catalyst compositions containing metallocenes and other Group 3–10 metal complexes are highly useful in the preparation of polyolefins, producing relatively homogeneous copolymers at excellent polymerization rates while allowing one to tailor closely the final properties of the product.

Certain metal complexes of tridentate, pyridine containing Schiff bases, such as those disclosed by Brookhart et al. are also known components of olefin polymerization catalysts, as disclosed in WO-A-98/27124, 98/30612, 99/02472, 99/12981, 00/69923 and EP-A-924,223. Organometallic compounds with other polydentate ligands are known in the scientific literature. See for examples: Fryzuk, *Can. J. Chem.*, vol. 70, p. 2839 (1992); Bochmann et al., *J. Chem. Soc., Dalton Trans.*, 459 (2000); Edwards, et al., *J. Chem. Soc., Dalton Trans.*, p. 1253 (1989); and van Koten, et al., *J. Am. Chem. Soc.*, vol. 104, p. 5490 (1982). However the teaching of these documents do not suggest that such compounds would show very high activity for the polymerization of olefins.

Despite advances in the present art, there remains a need for metal complexes having improved catalytic properties. It would be advantageous to be able to produce polyolefins with improved physical properties. It would also be especially advantageous to be able to produce crystalline polyolefins, particularly crystalline, isotactic polypropylene or poly(2-butene) using polymerization catalyst compositions that give polymers of high crystallinity and few chain defects. Such polymers possess extremely high strength properties, particularly at high use temperatures.

According to the present invention there are provided metal complexes comprising a multidentate chelating ligand, said metal complexes corresponding to the formula:

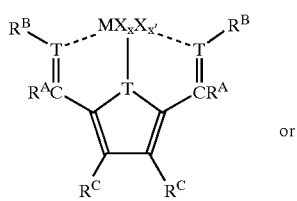

or

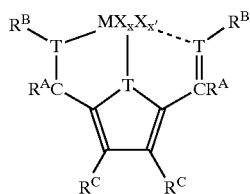

where M is a metal from one of Groups 3 to 13 of the Periodic Table of the Elements, the lanthanides or actinides;

T is nitrogen or phosphorus;

$R^A$ independently each occurrence is hydrogen, $R^B$ or $TR^B_j$, $R^B$ independently each occurrence is a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, and optionally the $R^B$ and $R^A$ groups bonded to the same T=C grouping may be joined together to form a divalent ligand group;

j is 1 or 2, and when j is 1, T' is oxygen or sulfur and when j is 2, T' is nitrogen or phosphorus, $R^C$ independently each occurrence is hydrogen or a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, or two $R^C$ groups are joined together forming a divalent ligand group;

X is an anionic ligand group having up to 60 atoms (excluding ligands that are cyclic, delocalized, π-bound ligand groups), and optionally two X groups together form a divalent ligand group;

X' independently each occurrence is a Lewis base ligand having up to 20 atoms;

x is a number from 0 to 5; and x' is zero, 1 or 2.

Also, according to the present invention, there is provided a catalyst composition for olefin polymerization comprising:
(A) a catalyst component comprising the foregoing metal complex; and
(B) a cocatalyst component comprising an activating cocatalyst wherein the molar ratio of (A) to (B) is from 1:10,000 to 100:1.

Further according to the present invention there is provided a process for the polymerization of olefins comprising contacting one or more $C_{2-20}$ α-olefins under polymerization conditions with one of the aforementioned catalyst compositions. A preferred process of this invention is a high temperature solution polymerization process for the polymerization of prochiral olefins comprising contacting one or more $C_{3-20}$ α-olefins under polymerization conditions with one of the aforementioned catalyst compositions at a temperature from 30 to 250° C., more preferably from 50 to 220° C., most preferably from 70 to 200° C.

In a further embodiment of the invention, there is provided a polymerization process for preparing isotactic polypropylene having an isotacticity as measured by $^{13}C$ NMR triads of greater than 75 percent, preferably greater than 85 percent, more preferably greater than 95 percent comprising contacting propylene at a temperature from 50 to 220° C., preferably from 70 to 200° C. under polymerization conditions with the foregoing catalyst composition.

Within the scope of this invention are the polyolefin and polypropylene products produced by the aforementioned processes. Preferred products have a high degree of crystallinity and relatively few polymer chain defects.

This invention also provides a compound capable of forming a multi-dentate chelating ligand, said compound corresponding to the formula:

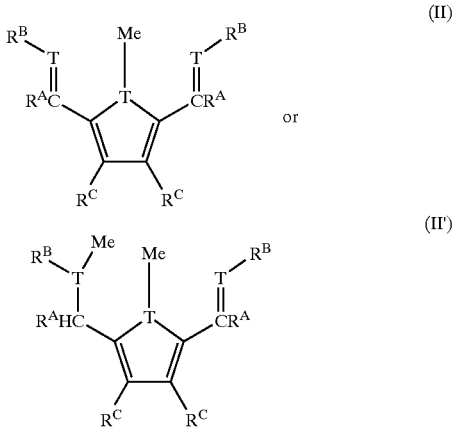

where $R^A$, $R^B$, and $R^C$, and T are as previously defined, and
Me is hydrogen, an alkali metal cation, an alkaline earth metal cation, or a Grignard cation. Thus, the compound may exist in the form of a free base capable of being deprotonated, a Group 1 or 2 metal salt, or a Group 2 metal halide salt.

Within the scope of this aspect of the invention is the use of one or more of the compounds of formula II or III for synthesis to produce a metal complex of formula (I) or (I') of this invention, or, more specifically, a process wherein one or more compounds of formula (II) or (II') are contacted with one or metal compounds of the formula, $X'_x$, $MX_{x+2}$, (IV) wherein M is a metal of Groups 3 to 13 of the Periodic Table of the Elements, the lanthanides or actinides, and X, x, X' and x' are as previously defined, under reaction conditions to form the desired metal complex of formula (I) or (I').

The present catalysts and processes may be used in the solution or bulk polymerization, slurry polymerization or gas phase polymerization of ethylene/propylene (EP polymers), ethylene/octene (EO polymers), ethylene/styrene (ES polymers), propylene homopolymers, copolymers of propylene with ethylene and/or $C_{4-10}$ α-olefins, and ethylene/propylene/diene (EPDM copolymers) wherein the diene is ethylidenenorbornene, 1,4-hexadiene or similar nonconjugated diene. As previously stated, the catalysts are especially desirable for use in the polymerization of propylene to give isotactic polypropylene of high isotacticity.

The catalysts of this invention may also be supported on a support material and used in olefin polymerization processes. The catalyst may also be prepolymerized with one or more olefin monomers in situ in a polymerization reactor or in a separate process with intermediate recovery of the prepolymerized catalyst prior to the primary polymerization process. Highly desirably, the catalyst compositions of the present invention produce highly isotactic polymers of prochiral α-olefins, especially, propylene, having tacticity (as measured by repeat mm diadds in the $^{13}C$ NMR spectrum) of greater than 95 percent, preferably greater than 96 percent. Further uniquely, the present invented polymerization process attains such highly isotactic polymers at polymerization temperatures greater than 70° C., preferably greater than 90° C. and the polymer has very low chain defects, preferably less than 0.1 mole percent, more preferably less than 0.01 mole percent. Such polymers are highly crystalline and have high crystalline melting points due to the uniform nature of the polymer chains.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups. The full teachings of any patent, patent application, provisional application, or publication referred to herein are hereby incorporated by reference for purpose of United States Patent practice. The term "comprising" when used herein with respect to a composition or mixture is not intended to exclude the additional presence of any other compound or component. In the structural formulas appearing herein, a dashed line or an arrow indicates a coordinate covalent bond formed from a donor pair of electrons.

Olefins as used herein are $C_{2-20}$ aliphatic or aromatic compounds containing vinylic unsaturation, as well as cyclic compounds such as cyclobutene, cyclopentene, and norbornene, including norbornene substituted in the 5- and 6-positions with $C_{1-20}$ hydrocarbyl groups. Also included are mixtures of such olefins as well as mixtures of such olefins with $C_{4-20}$ diolefin compounds. Examples of the latter compounds include ethylidene norbornene, 1,4-hexadiene, and norbornadiene. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a nonconjugated diene, such as, for example, EPDM terpolymers.

Illustrative $TR^B_j$ groups include methoxy, ethoxy, propoxy, methylethyloxy, 1,1-dimethyethyloxy, trimethylsiloxy, 1,1-dimethylethyl(dimethylsilyl)oxy, dimethylamino, diethylamino, methylethylamino, methylphenylamino, dipropylamino, dibutylamino, 2,6-diisopropylphenylamino, 2,6-dit-butylphenylamino, phenylamino, piperidino, morpholino, pyrrolidino, hexahydro-1H-azepin-1-yl, hexahydro-1(2H)-azocinyl, octahydro-1H-azonin-1-yl or octahydro-1(2H)-azecinyl, or two adjacent $TR^B_j$ groups are —OCH$_2$O—. More preferred are those wherein the $R^B_jT$ group is 2,6-diisopropylphenylamino, 2,6-dit-butylphenylamino, phenylamino, dimethylamino, methylphenylamino, piperidino or pyrrolidino.

Preferred X groups are halide, hydrocarbyl (including alkyl, alkenyl, aryl, alkaryl, aralkyl cycloalkyl and cycloalkenyl) hydrocarbyloxide, hydrocarbylsulfide, N,N-dihydrocarbylamide, hydrocarbyleneamide, hydrocarbylcarboxylate, acetylacetonate, cyano, dithiocarbamate, and dithiocarboxylate groups, said X having from 1 to 20 atoms other than hydrogen.

Preferred X' groups are carbon monoxide; phosphines, especially trimethylphosphine, triethylphosphine, triphenylphosphine and bis(1,2-dimethylphosphino)ethane; $P(OR^i)_3$, wherein $R^i$ is hydrocarbyl, silyl or a combination thereof, ethers, especially tetrahydrofuran; amines, especially pyridine, bipyridine, tetramethylethylenediamine (TMEDA), and triethylamine; olefins; and conjugated dienes having from 4 to 40 carbon atoms. Complexes including the latter X' groups include those wherein the metal is in the +2 formal oxidation state.

More preferred $R^A$ groups are hydrogen, alkyl, aryl, aralkyl, alkoxy, dihydrocarbylamino, and hydrocarbyleneamino, said $R^A$ group having from 1 to 20 nonhydrogen atoms, most preferably hydrogen, alkyl, aryl, N,N-dimethylamino and pyrrolidino.

Preferred coordination complexes according to the present invention are complexes corresponding to the formula I:

where M is a metal of Groups 4–8; preferably titanium, zirconium, vanadium, iron or chromium; most preferably zirconium T is nitrogen;

X is chloride or $C_{1-10}$ hydrocarbyl; and x' is zero.

More preferably independently each occurrence $R^A$ is hydrogen, methyl or phenyl, $R^B$ is aryl or alkyl substituted aryl, and $R^C$ is hydrogen.

Most highly preferred complexes correspond to the formula:

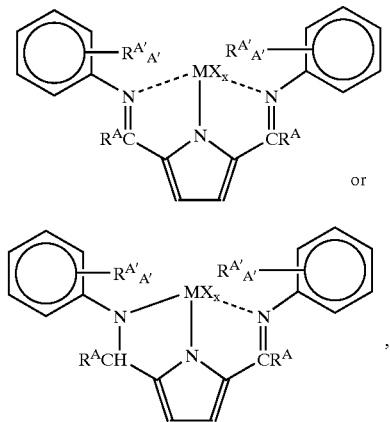

IA or

I'A wherein $R^{A'}$ independently each occurrence is $C_{1-4}$ alkyl, most preferably methyl, isopropyl, or t-butyl, A' is 0, 1 or 2; $R^A$ is hydrogen, or $C_{1-10}$ hydrocarbyl, M is zirconium, vanadium or chromium; especially zirconium, X is halide or $C_{1-10}$ hydrocarbyl, and x is 1 or 2.

In a particularly preferred embodiment of the invention, the metal complex corresponds to the formula:

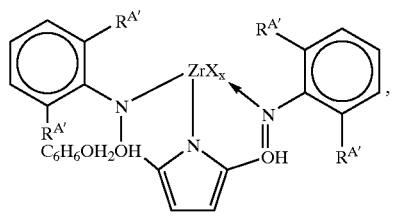

I'B wherein $R^{A'}$ independently each occurrence is methyl, isopropyl or t-butyl, X is benzyl, and x is 2.

The metal compounds of formula (IV) for use herein is preferably a metal hydrocarbyl, metal halide, metal silyla- lkyl, metal amide, or metal phosphide. Examples of useful metal compounds are tetramethylzirconium, tetrakis (trimethylsilylmethyl)zirconium, tetrakis(dimethylamino)zirconium, dichlorodibenzylzirconium, bis(dimethylamino)-bisbenzylzirconium, tetrabenzylzirconium;

tetramethylhafnium, tetratethylhafnium, tetrakis(trimethylsilylmethyl)hafnium, tetrakis(dimethylamino) hafnium, dichlorodibenzylhafnium, chlorotribenzylhafnium, trichlorobenzylhafnium, bis(dimethylamino) bisbenzylhafnium, tetrabenzylhafnium;

tetramethyltitanium, tetratethyltitanium, tetrakis(trimethylsilylmethyl)titanium, tetrakis(dimethylamino))titanium, dichlorodibenzyltitanium, chlorotribenzyltitanium, trichlorobenzyltitanium, bis(dimethylamino)bis (benzyl)titanium, tetrabenzyl titanium;

tetrakis(trimethylsilylmethyl)chromium, tetramethylchromium, tetrabenzylchromium, tetrakis(neopentyl)chromium, tetrakis(neophyl)chromium, and tetrakis(tritylmethyl)chromium;

tetrakis(trimethylsilylmethyl)vanadium, tetrabenzylvanadium, tetrakis((trimethlsilyl)methyl) vanadium, tetrakis (neophyl)vanadium, and tetrakis(tritylmethyl)chromium;

tetrakis(tertbutyl)lanthanium; lithiumhexamethyllanthanium; tetrakis(allyl)lanthanium, and tri(bis(trimethylsilyl)methyl)lanthanium.

Preferred metal compounds of formula (IV) are $C_{1-10}$ metal alkyl, metal aryl, or metal arylalkyl compounds. Highly preferably the metal compound of formula (IV) is a zirconium hydrocarbyl, most preferably tetrabenzylzirconium.

Formation of the polydentate chelating ligands and ultimately the metal complexes themselves uses conventional organic- and organometallic-synthetic procedures. The reactions are conducted in a suitable noninterfering solvent at a temperature from −100 to 300° C., preferably from −78 to 100° C., most preferably from 0 to 50° C.

Suitable reaction media for the formation of the polydentate chelating ligands and complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

The complexes are rendered catalytically active by combination with an activating cocatalyst or use of an activating technique, such as those that are previously known in the art for use with Group 4 metal olefin polymerization complexes. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. A preferred ion forming compound is a tri($C_{1-20}$-hydrocarbyl)ammonium salt of a tetrakis(fluoroaryl)borate, especially a tetrakis(pentafluorophenyl)borate. The foregoing activating cocatalysts and activating techniques have been previously taught with respect to different metal complexes in the following references: EP-A-277,003, U.S. Pat. No. 5,153,157, U.S. Pat. No. 5,064,802, U.S. Pat. No. 5,321,106, U.S. Pat. No. 5,721,185, U.S. Pat. No. 5,350,723, U.S. Pat. No. 5,425,872, U.S. Pat. No. 5,625,087, U.S. Pat. No. 5,883,204, U.S. Pat. No. 5,919,983, U.S. Pat. No. 5,783,512, WO 99/15534, and U.S. Ser. No. 09/251,664, filed Feb. 17, 1999 (WO99/42467).

Combinations of neutral Lewis acids, especially the combination of a trialkylaluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluoro-phenylborane:alumoxane are from 1:1:1 to 1:10:30, more preferably from 1:1:1.5 to 1:5:10.

Suitable ion forming compounds useful as cocatalysts in one embodiment of the present invention comprise a cation which is a Brønsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gallium, niobium or tantalum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$$(L^*-H)_d^+(A)^{d-}$$

wherein:
L* is a neutral Lewis base;
$(L^*-H)^+$ is a conjugate Brønsted acid of L*;
$A^{d-}$ is a noncoordinating, compatible anion having a charge of d−, and
d is an integer from 1 to 3.
More preferably $A^{d-}$ corresponds to the formula: $[M'Q_4]^-$;
wherein:
M' is boron or aluminum in the +3 formal oxidation state; and
Q independently each occurrence is selected from hydride, dialkylamido, halide, hydrocarbyl, hydrocarbyloxide, halo-substituted hydrocarbyl, halo-substituted hydrocarbyloxy, and halo-substituted silylhydrocarbyl radicals (including perhalogenated hydrocarbyl- perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is $A^-$. Activating cocatalysts comprising boron which are particularly useful in the preparation of catalysts of this invention may be represented by the following general formula:

$$(L^*-H)^+(BQ_4)^-;$$

wherein:
L* is as previously defined;
B is boron in a formal oxidation state of 3; and
Q is a hydrocarbyl-, hydrocarbyloxy-, fluorohydrocarbyl-, fluorohydrocarbyloxy-, hydroxyfluorohydrocarbyl-, dihydrocarbylaluminumoxyfluorohydrocarbyl-, or fluorinated silylhydrocarbyl- group of up to 20 nonhydrogen atoms, with the proviso that in not more than one occasion is Q hydrocarbyl. Most preferably, Q is each occurrence a fluorinated aryl group, especially, a pentafluorophenyl group.

Preferred Lewis base salts are ammonium salts, more preferably trialkyl-ammonium- or dialkylarylammonium-salts containing one or more $C_{12-40}$ alkyl groups. The latter cocatalysts have been found to be particularly suitable for use in combination with not only the present metal complexes but other Group 4 metallocenes as well.

Illustrative, but not limiting, examples of boron compounds which may be used as an activating cocatalyst in the preparation of the improved catalysts of this invention (as well as previously known Group 4 metal catalysts) are tri-substituted ammonium salts such as:
trimethylammonium tetrakis(pentafluorophenyl) borate,
triethylammonium tetrakis(pentafluorophenyl) borate,
tripropylammonium tetrakis(pentafluorophenyl) borate,
tri(n-butyl)ammonium tetrakis(pentafluorophenyl) borate,
tri(sec-butyl)ammonium tetrakis(pentafluorophenyl) borate,
N,N-dimethylanilinium tetrakis(pentafluorophenyl) borate,
N,N-dimethylanilinium n-butyltris(pentafluorophenyl) borate,
N,N-dimethylanilinium benzyltris(pentafluorophenyl) borate,
N,N-dimethylanilinium tetrakis(4-(t-butyldimethylsilyl)-2,3,5,6-tetrafluorophenyl) borate,
N,N-dimethylanilinium tetrakis(4-(triisopropylsilyl)-2,3,5,6-tetrafluorophenyl) borate,
N,N-dimethylanilinium pentafluorophenoxytris(pentafluorophenyl) borate, N,N-diethylanilinium tetrakis(pentafluorophenyl) borate,
N,N-dimethyl-2,4,6-trimethylanilinium tetrakis(pentafluorophenyl) borate,
dimethyltetradecylammonium tetrakis(pentafluorophenyl) borate,
dimethylhexadecylammonium tetrakis(pentafluorophenyl) borate,
dimethyloctadecylammonium tetrakis(pentafluorophenyl) borate,
methylditetradecylammonium tetrakis(pentafluorophenyl) borate,
methylditetradecylammonium (hydroxyphenyl)tris(pentafluorophenyl) borate,
methylditetradecylammonium (diethylaluminoxyphenyl)tris(pentafluorophenyl) borate,
methyldihexadecylammonium tetrakis(pentafluorophenyl) borate,
methyldihexadecylammonium (hydroxyphenyl)tris(pentafluorophenyl) borate,
methyldihexadecylammonium (diethylaluminoxyphenyl) tris(pentafluorophenyl) borate,
methyldioctadecylammonium tetrakis(pentafluorophenyl) borate,
methyldioctadecylammonium (hydroxyphenyl)tris(pentafluorophenyl) borate,
methyldioctadecylammonium (diethylaluminoxyphenyl)tris(pentafluorophenyl) borate,
methyldioctadecylammonium tetrakis(pentafluorophenyl) borate,
phenyldioctadecylammonium tetrakis(pentafluorophenyl) borate,
phenyldioctadecylammonium (hydroxyphenyl)tris(pentafluorophenyl) borate,
phenyldioctadecylammonium (diethylaluminoxyphenyl)tris(pentafluorophenyl) borate,
(2,4,6-trimethylphenyl)dioctadecylammonium tetrakis(pentafluophenyl) borate
(2,4,6-trimethylphenyl)dioctadecylammonium (hydroxyphenyl)tris(pentafluorophenyl)-borate,
(2,4,6-trimethylphenyl)dioctadecylammonium (diethylaluminoxyphenyl) tris(pentafluorophenyl)borate,
(2,4,6-trifluorophenyl)dioctadecylammonium tetrakis(pentafluorophenyl)borate,
(2,4,6-trifluorophenyl)dioctadecylammonium (hydroxyphenyl)tris(pentafluorophenyl)-borate,
(2,4,6-trifluorophenyl)dioctadecylammonium (diethylaluminoxyphenyl)tris(pentafluorophenyl) borate,
(pentafluorophenyl)dioctadecylammonium tetrakis(pentafluorophenyl)borate,
(pentafluorophenyl)dioctadecylammonium (hydroxyphenyl)tris(pentafluorophenyl)-borate,
(pentafluorophenyl)dioctadecylammonium (diethylaluminoxyphenyl)tris(pentafluoro-phenyl) borate,
(p-trifluoromethylphenyl)dioctadecylammonium tetrakis(pentafluorophenyl)borate,
(p-trifluoromethylphenyl)dioctadecylammonium (hydroxyphenyl)tris(pentafluoro-phenyl) borate,
(p-trifluoromethylphenyl)dioctadecylammonium (diethylaluminoxyphenyl)tris(pentafluorophenyl) borate,
p-nitrophenyldioctadecylammonium tetrakis(pentafluorophenyl)borate,
p-nitrophenyldioctadecylammonium (hydroxyphenyl)tris(pentafluorophenyl) borate,
p-nitrophenyldioctadecylammonium (diethylaluminoxyphenyl)tris(pentafluorophenyl) borate, and mixtures of the foregoing, dialkyl ammonium salts such as:
di-(i-propyl)ammonium tetrakis(pentafluorophenyl) borate,
methyloctadecylammonium tetrakis(pentafluorophenyl) borate,
methyloctadodecylammonium tetrakis(pentafluorophenyl) borate, and
dioctadecylammonium tetrakis(pentafluorophenyl) borate;
tri-substituted phosphonium salts such as:
triphenylphosphonium tetrakis(pentafluorophenyl) borate,
methyldioctadecylphosphonium tetrakis(pentafluorophenyl) borate, and
tri(2,6-dimethylphenyl)phosphonium tetrakis(pentafluorophenyl) borate;
di-substituted oxonium salts such as:
diphenyloxonium tetrakis(pentafluorophenyl) borate,
di(o-tolyl)oxonium tetrakis(pentafluorophenyl) borate, and
di(octadecyl)oxonium tetrakis(pentafluorophenyl) borate;
di-substituted sulfonium salts such as:
di(o-tolyl)sulfonium tetrakis(pentafluorophenyl) borate, and
methylcotadecylsulfonium tetrakis(pentafluorophenyl) borate.

Preferred trialkylammonium cations are methyldioctadecylammonium and dimethyloctadecylammonium. The use of the above Brønsted acid salts as activating cocatalysts for addition polymerization catalysts is known in the art, having been disclosed in U.S. Pat. Nos. 5,064,802, 5,919,983, 5,783,512 and elsewhere. Preferred dialkylarylammonium cations are fluorophenyldioctadecylammonium-, perfluorophenyldioctacecylammonium- and p-trifluoromethylphenyldi(octadecyl)ammonium cations. It should be noted that certain of the cocatalysts, especially those containing a hydroxyphenyl ligand in the borate anion, may require the addition of a Lewis acid, especially a trialkylaluminum compound, to the polymerization mixture or the catalyst composition, in order to form the active catalyst composition.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:
$Ox^{e+}$ is a cationic oxidizing agent having a charge of e+;
e is an integer from 1 to 3; and
$A^{d-}$ and d are as previously defined.

Examples of cationic oxidizing agents include: ferrocenium, hydrocarbyl-substituted ferrocenium, $Ag^{+}$ or $Pb^{+2}$. Preferred embodiments of $A^{d-}$ are those anions previously defined with respect to the Brønsted acid containing activating cocatalysts, especially tetrakis(pentafluorophenyl) borate. The use of the above salts as activating cocatalysts for addition polymerization catalysts is known in the art, having been disclosed in U.S. Pat. No. 5,321,106.

Another suitable ion forming, activating cocatalyst comprises a compound which is a salt of a carbenium ion and a noncoordinating, compatible anion represented by the formula:

$$©^{+}A^{-}$$

wherein:
$©^{+}$ is a $C_{1-20}$ carbenium ion; and
$A^{-}$ is as previously defined. A preferred carbenium ion is the trityl cation, that is triphenylmethylium. The use of the above carbenium salts as activating cocatalysts for addition polymerization catalysts is known in the art, having been disclosed in U.S. Pat. No. 5,350,723.

A further suitable ion forming, activating cocatalyst comprises a compound which is a salt of a silylium ion and a noncoordinating, compatible anion represented by the formula:

$$R^3{}_3Si(X')_q{}^+A^-$$

wherein:

$R^3$ is $C_{1-10}$ hydrocarbyl, and X', q and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. The use of the above silylium salts as activating cocatalysts for addition polymerization catalysts is known in the art, having been disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Another class of suitable catalyst activators are expanded anionic compounds corresponding to the formula: $(A^{1+a^1})_{b^1}(Z^1J^1{}_j{}^1)^{-c^1}{}_{d^1}$, wherein:

$A^1$ is a cation of charge $+a^1$, $Z^1$ is an anion group of from 1 to 50, preferably 1 to 30 atoms, not counting hydrogen atoms, further containing two or more Lewis base sites;

$J^1$ independently each occurrence is a Lewis acid coordinated to at least one Lewis base site of $Z^1$, and optionally two or more such $J^1$ groups may be joined together in a moiety having multiple Lewis acidic functionality, $j^1$ is a number from 2 to 12 and $a^1$, $b^1$, $c^1$, and $d^1$ are integers from 1 to 3, with the proviso that $a^1 \times b^1$ is equal to $c^1 \times d^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

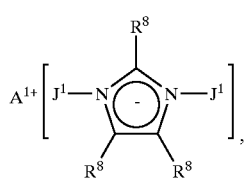
,

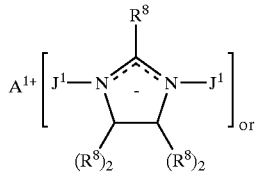
or

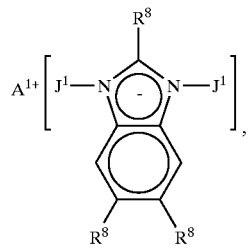
, wherein:

$A^{1+}$ is a monovalent cation as previously defined, and preferably is a trihydrocarbyl ammonium cation, containing one or two $C_{10-40}$ alkyl groups, especially the methylbis(tetradecyl)ammonium- or methylbis(octadecyl)ammonium-cation, $R^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^1$ is tris(pentafluorophenyl)borane or tris(pentafluorophenyl)aluminane.

Examples of these catalyst activators include the trihydrocarbylammonium-, especially, methylbis(tetradecyl)ammonium- or methylbis(octadecyl)ammonium-salts of:

bis(tris(pentafluorophenyl)borane)imidazolide,
bis(tris(pentafluorophenyl)borane)-2-undecylimidazolide,
bis(tris(pentafluorophenyl)borane)-2-heptadecylimidazolide, bis(tris(pentafluorophenyl)borane)-4,5 -bis(undecyl)imidazolide,
bis(tris(pentafluorophenyl)borane)-4,5-bis(heptadecyl)imidazolide,
bis(tris(pentafluorophenyl)borane)imidazolinide,
bis(tris(pentafluorophenyl)borane)-2-undecylimidazolinide,
bis(tris(pentafluorophenyl)borane)-2-heptadecylimidazolinide,
bis(tris(pentafluorophenyl)borane)-4,5-bis(undecyl)imidazolinide,
bis(tris(pentafluorophenyl)borane)-4,5-bis(heptadecyl)imidazolinide,
bis(tris(pentafluorophenyl)borane)-5,6-dimethylbenzimidazolide,
bis(tris(pentafluorophenyl)borane)-5,6-bis(undecyl)benzimidazolide,
bis(tris(pentafluorophenyl)alumane)imidazolide,
bis(tris(pentafluorophenyl)alumane)-2-undecylimidazolide,
bis(tris(pentafluorophenyl)alumane)-2-heptadecylimidazolide,
bis(tris(pentafluorophenyl)alumane)-4,5-bis(undecyl)imidazolide,
bis(tris(pentafluorophenyl)alumane)-4,5-bis(heptadecyl) imidazolide,
bis(tris(pentafluorophenyl)alumane)imidazolinide,
bis(tris(pentafluorophenyl)alumane)-2-undecylimidazolinide,
bis(tris(pentafluorophenyl)alumane)-2-heptadecylimidazolinide,
bis(tris(pentafluorophenyl)alumane)-4,5-bis(undecyl)imidazolinide,
bis(tris(pentafluorophenyl)alumane)-4,5-bis(heptadecyl) imidazolinide,
bis(tris(pentafluorophenyl)alumane)-5,6-dimethylbenzimidazolide, and bis(tris(pentafluorophenyl)alumane)-5,6-bis(undecyl)benzimidazolide.

A further class of suitable activating cocatalysts include cationic Group 13 salts corresponding to the formula:

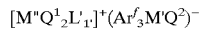

wherein:

M" is aluminum, gallium, or indium;

M' is boron or aluminum;

$Q^1$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^1$ groups may be covalently linked with each other to form one or more fused rings or ring systems;

$Q^2$ is an alkyl group, optionally substituted with one or more cycloalkyl or aryl groups, said $Q^2$ having from 1 to 30 carbons;

L' is a monodentate or polydentate Lewis base, preferably L' is reversibly coordinated to the metal complex such that it may be displaced by an olefin monomer, more preferably L' is a monodentate Lewis base;

1' is a number greater than zero indicating the number of Lewis base moieties, L', and $Ar^f$ independently each occurrence is an anionic ligand group; preferably $Ar^f$ is selected from the group consisting of halide, $C_{1-20}$ halohydrocarbyl, and $Q^1$ ligand groups, more preferably $Ar^f$ is a fluorinated hydrocarbyl moiety of from 1 to 30 carbon atoms, most preferably $Ar^f$ is a fluorinated aromatic hydrocarbyl moiety of from 6 to 30 carbon atoms, and most highly preferably $Ar^f$ is a perfluorinated aromatic hydrocarbyl moiety of from 6 to 30 carbon atoms.

Examples of the foregoing Group 13 metal salts are alumicinium tris(fluoroaryl)borates or gallicinium tris(fluoroaryl)borates corresponding to the formula: $[M"Q^1{}_2L'{}_{1'}]^+(Ar^f{}_3BQ^2)^-$, wherein M" is aluminum or gallium; $Q^1$ is $C_{1-20}$ hydrocarbyl, preferably $C_{1-8}$ alkyl; $Ar^f$ is perfluoroaryl, preferably pentafluorophenyl; and $Q^2$ is $C_{1-8}$ alkyl, preferably $C_{1-8}$ alkyl. More preferably, $Q^1$ and $Q^2$ are identical $C_{1-8}$ alkyl groups, most preferably, methyl, ethyl or octyl.

The foregoing activating cocatalysts may also be used in combination. An especially preferred combination is a mixture of a tri(hydrocarbyl)aluminum or tri(hydrocarbyl)borane compound having from 1 to 4 carbons in each hydrocarbyl group or an ammonium borate with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalysts, whether or not supported in any suitable manner, may be used to polymerize ethylenically unsaturated monomers having from 2 to 100,000 carbon atoms either alone or in combination. Preferred addition polymerizable monomers for use herein include olefins, diolefins and mixtures thereof. Preferred olefins are aliphatic or aromatic compounds containing vinylic unsaturation as well as cyclic compounds containing ethylenic unsaturation. Examples of the latter include cyclobutene, cyclopentene, norbornene, and norbornene derivatives that are substituted in the 5- and 6-positions with $C_{1-20}$ hydrocarbyl groups. Preferred diolefins are $C_{4-40}$ diolefin compounds, including ethylidene norbornene, 1,4-hexadiene, and norbornadiene. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a nonconjugated diene, such as, for example, EPDM terpolymers.

Most preferred monomers include the $C_{2-20}$ α-olefins, especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

Preferred monomers include a combination of ethylene, propylene, and mixtures of ethylene with one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a nonconjugated diene, especially ethylidenenorbornene or 1,4-hexadiene.

In general, the polymerization may be accomplished at conditions well known in the prior art for solution phase, slurry, gas phase and high pressure Ziegler-Natta or Kaminsky-Sinn type polymerization reactions. Examples of such well known polymerization processes are depicted in U.S. Pat. No. 5,084,534, U.S. Pat. No. 5,405,922, U.S. Pat. No. 4,588,790, U.S. Pat. No. 5,032,652, U.S. Pat. No. 4,543,399, U.S. Pat. No. 4,564,647, U.S. Pat. No. 4,522,987, and elsewhere. Preferred polymerization pressures are from atmospheric to 3000 atmospheres. Molecular weight control agents can be used in combination with the present cocatalysts. Examples of such molecular weight control agents include hydrogen, silanes or other known chain transfer agents. The catalyst composition may be used by itself (homogeneously) or supported on a support material. Suitable support materials include metal halides, metal oxides, metal nitrides, metalloid oxides, metalloid carbides, clays and polymeric hydrocarbons. Preferred supports include silica, alumina, aluminosilicates, clays, borosilicates, boron nitrides, boron carbides, mixed oxides of magnesium and aluminum and/or silicon, including expanded clay materials, and the foregoing materials having residual hydroxyl groups thereof reacted with trialkyl aluminum compounds.

The catalyst composition (whether based on a catalyst complex or catalyst compound) may further comprise an electron donor compound which may interact with either the metal complex or metal compound, the support, or the combination of the metal complex and support or metal compound and support to give improved (greater quantity) of isospecific polymer formation. Suitable electron donors include both internal donor and external donors. Specific examples include alkyl esters- or alkyl diesters- of aromatic acids, especially $C_{1-4}$ alkylbenzoates, most especially ethylbenzoate, or $C_{1-4}$ dialkylphthalates, most especially dibutyl phthalate; and alkylsiloxanes, especially phenyl triethyloxysilane. Electron donors are previously known in the art for improved isoselective polymer formation, and have been discussed in K. Soga, et al., *Prog. Polym. Sci.* 22, 1503–1546, (1997), and elsewhere. In most polymerization reactions the molar ratio of catalyst:polymerizable compounds employed is from $10^{-12}:1$ to $10^{-1}:1$, more preferably from $10^{-9}:1$ to $10^{-5}:1$.

The catalyst composition or the respective components thereof may be impregnated onto a solid, inert support, used in a liquid form such as a solution, dispersion or neat liquid, or it may be spray dried, or formed in situ during polymerization. Particularly preferred among these is a catalyst composition that is spray dried as described in EP-A-668, 295 or used in the form of a liquid, such as is described in U.S. Pat. No. 5,317,036.

In the case of a supported catalyst composition, the catalyst composition may be impregnated in or deposited on the surface a porous, inert substrate, such as silica, carbon black, polyethylene, polycarbonate, polystyrene, alumina, zirconia, or a magnesium halide (especially magnesium dichloride), such that the catalyst composition is between 0.001 and 1.0 percent by weight of the total weight of the catalyst composition and the support.

The olefin polymerization catalyst may be used in slurry, liquid phase, gas phase and liquid monomer-type reaction systems as are known in the art for polymerizing olefins. Polymerization preferably is conducted in a fluidized bed polymerization reactor, however, by continuously contacting an alpha-olefin having 2 to 8 carbon atoms with the components of the catalyst system, that is, the procatalyst component and cocatalyst. In accordance with the process, discrete portions of the catalyst components can be continually fed to the reactor in catalytically effective amounts together with the alpha-olefin while the polymer product is continually removed during the continuous process. Fluidized bed reactors suitable for continuously polymerizing alpha-olefins have been previously described and are well known in the art. Fluidized bed reactors useful for this purpose are described in U.S. Pat. Nos. 4,302,565, 4,302,566, 4,303,771, and elsewhere.

It is preferred sometimes that such fluidized beds are operated using a recycle stream of unreacted monomer from the fluidized bed reactor. In this context, it is preferred to condense at least a portion of the recycle stream. Alternatively, the recycle may include a deliberately added, inert, vaporizable, liquid condensing agent. This is known in the art as operating in "condensing mode." Operating a fluidized bed reactor in condensing mode generally is known in the art and described in, for example, U.S. Pat. Nos. 4,543,399 and 4,588,790 and elsewhere. The use of condensing mode has been found to lower the amount of xylene soluble, low molecular weight species, especially in the formation of isotactic polypropylene. The procedure also may be employed to improve catalyst performance when using the catalyst of the present invention.

The catalyst composition may be used for the polymerization of olefins by any suspension, solution, slurry, or gas phase process, using known equipment and reaction conditions, and is not limited to any specific type of reaction system. Generally, olefin polymerization temperatures range from 0° C. to 200° C. at atmospheric, subatmospheric, or superatmospheric pressures. Slurry or solution polymerization processes may utilize subatmospheric or superatmospheric pressures and temperatures in the range of 40° C. to 110° C. A useful liquid phase polymerization reaction system is described in U.S. Pat. No. 3,324,095. Liquid phase reaction systems generally comprise a reactor vessel to which olefin monomer and catalyst composition are added, and which contains a liquid reaction medium for dissolving or suspending the polyolefin. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are isopentane, hexane, cyclohexane, heptane, benzene, toluene, and ethylbenzene. Reactive contact between the olefin monomer and the catalyst composition should be maintained by constant stirring or agitation. The reaction medium containing the olefin polymer product and unreacted olefin monomer is withdrawn from the reactor continuously or semi-continuously. The olefin polymer product is separated, and the unreacted olefin monomer and liquid reaction medium are recycled into the reactor.

Preferably, gas phase polymerization is employed, with superatmospheric pressures in the range of 1 to 1000 psig (100 kPa–7 MPa), preferably 50 to 400 psig (340 kPa–2.8 MPa), most preferably 100 to 300 psig (700 kPa–2.0 MPa), and temperatures in the range of 30 to 130° C., preferably 65 to 110° C. Stirred or fluidized bed gas phase reaction systems are particularly useful. Generally, a conventional gas phase, fluidized bed process is conducted by passing a stream containing one or more olefin monomers continuously through a fluidized bed reactor under reaction conditions and in the presence of catalyst composition at a velocity sufficient to maintain a bed of solid particles in a suspended condition. A stream containing unreacted monomer is withdrawn from the reactor continuously, compressed, cooled, optionally fully or partially condensed as disclosed in U.S. Pat. Nos. 4,588,790 and 5,462,999, and recycled to the reactor. Product is withdrawn from the reactor and make-up monomer is added to the recycle stream. As desired for temperature control of the system, any gas inert to the catalyst composition and reactants may also be present in the gas stream. In addition, a fluidization aid such as carbon black, silica, clay, or talc may be used, as disclosed in U.S. Pat. No. 4,994,534.

Polymerization may be carried out in a single reactor or in two or more reactors in series, and is conducted substantially in the absence of catalyst poisons. Organometallic compounds may be employed as scavenging agents for poisons to increase the catalyst activity. Examples of scavenging agents are metal alkyls, preferably aluminum alkyls, most preferably triisobutylaluminum. When aluminoxane is used as an activator, any excess over the amount needed to activate the catalysts will act as scavenger compounds and additional scavenging may not be necessary.

Conventional additives may be included in the process, provided they do not interfere with the operation of the catalyst composition in forming the desired polyolefin. Hydrogen or a metal or a non-metal hydride, for example, a silyl hydride, may be used as a chain transfer agent in the process. Hydrogen may be used in amounts up to 10 moles of hydrogen per mole of total monomer feed. Also, as desired for temperature control of the system, any gas inert to the catalyst composition and reactants can also be present in the gas stream.

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. Where stated, the term "room temperature" refers to a temperature from 20 to 25° C., the term "overnight" refers to a time from 12 to 18 hours. All reagents were purchased or prepared according to published techniques. All syntheses were performed under dry nitrogen or argon atmospheres using a combination of glove box and high vacuum techniques at room temperature unless indicated otherwise.

EXAMPLES

The following defined terms will be used in the examples.

Density in g/ml was determined in accordance with ASTM 1505, based on ASTM D-1928, procedure C, plaque preparation. A plaque was made and conditioned for one hour at 100° C. to approach equilibrium crystallinity, measurement for density was then made in a density gradient column.

MAO is a solution of methyl aluminoxane (type 3 Å) in toluene, approximately 2.3 molar in aluminum, available from Akzo Corporation.

BBF is Butyl Branching Frequency, number of butyl branches per 1000 main chain carbon atoms based Nuclear Magnetic Resonance techniques.

PDI stands for Polydispersity Index, which is equivalent to Molecular Weight Distribution ($M_w/M_n$). PDI was determined by gel permeation chromatography using crosslinked polystyrene columns; pore size sequence: 1 column less than 1000 Å, 3 columns of mixed $5 \times 10^7$ Å; 1,2,4-trichlorobenzene solvent at 140° C. with refractive index detection.

Mn is number average Molecular Weight, as determined by gel permeation chromatography using crosslinked polystyrene columns.

FI is the flow index (optionally termed $I_{21}$), reported as grams per 10 minutes, determined in accordance with ASTM D-1238 condition F, and was measured at ten times the weight used in the melt index test.

MFR is the melt flow ratio, which is the ratio of flow index to melt index. It is related to the molecular weight distribution of the polymer.

PDI is Polydispersity Index, equivalent to Molecular Weight Distribution (Mw/Mn).

Activity is given in g polymer/mmol Zr/hour/100 psi (700 kPa) ethylene.

Example 1

Preparation of 2,5-Bis((2,6-diisopropylphenyl)aldimino)pyrrole

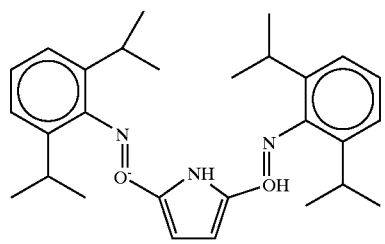

A reaction mixture containing pyrrole-2,5-dicarboxaldehyde (1.9 g; 15 mmol), 2 equivalents of 2,6-diisopropylaniline (36 mmol; 7.5 mL), several drops of formic acid (0.5 mL) and methanol (50 mL) was allowed to stir overnight. The bright yellow solid which had precipitated from solution was collected by filtration onto a fritted disk and dried under reduced pressure. The solid was then extracted into a minimal volume of hexane and dried over magnesium sulfate. After removal of the volatiles the desired complex was collected as a yellow solid. Formation of the desired product was confirmed by $^1$H NMR, mass spectrometry, and $^{13}$C NMR analysis.

Example 2

Preparation of 2,5-Bis((2,6-dimethylphenyl)aldimino)pyrrole

The reaction conditions of Example 1 were substantially repeated, excepting that 2,6-dimethylaniline was substituted 2,6-diisopropylaniline. Formation of the desired product was confirmed by $^1$H NMR, mass spectrometry, and $^{13}$C NMR analysis.

Example 3

Preparation of [(2-(2,6-diisopropylphenyl)iminomethyl)-5-( 2,6-diisopropylphenyl)amido(benzyl)methyl)pyrrol-1-yl]Zr dibenzyl

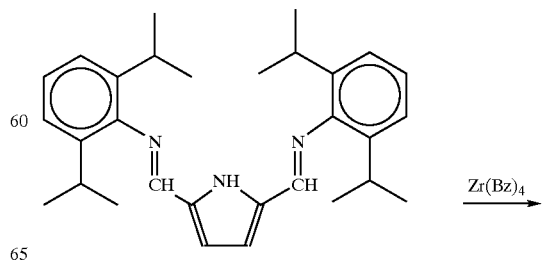

-continued

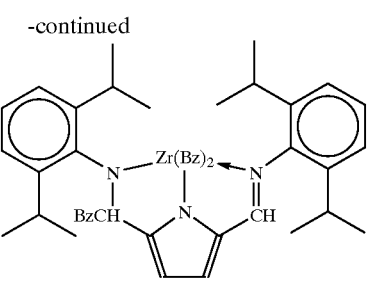

In the glove box in the dark, a round bottom flask was charged with 232 mg (2,5-bis((2,6-diisopropylphenyl)aldimino)pyrrole) (0.527 mmol, Example 1) and 50 mL toluene. The solution was cooled to −37° C. and then 229 mg $Zr(CH_2C_6H_5)_4$ ( 0.502 mmol) in 5 mL toluene was added to the pre-cooled solution. The reaction mixture was allowed to warm to room temperature. After stirring for 4 h, the solution was filtered using diatomaceous earth filter aid and concentrated to approximately 10 mL. Hexane (50 mL) was carefully layered on top of the toluene and the solution was left overnight. The bright orange solid which formed were collected onto a fritted disk and dried under reduced pressure. Formation of the desired product was accompanied by formation of toluene and the product's identity was confirmed by $^1$H NMR, mass spectrometry, and $^{13}$C NMR analysis.

Polymerization 1

A series of ethylene/hexene copolymers were made in a laboratory scale, one liter autoclave reactor using the metal complex described in Example 3 and MAO cocatalyst or tris(pentafluorophenyl)boron cocatalyst (with MAO scavenger separately added to the reactor). In each case excepting Run 4, the catalyst combination was prepared by combining a solution of the metal complex with a portion of the MAO (~50equivalents) solution and retaining the resultant catalyst composition at room temperature for 10 minutes prior to injection into the reactor. Reaction conditions and results are shown in Table 1 below.

TABLE 1

| Run | mmol Zr | Al/Zr mole ratio | T (° C.) | H$_2$ (cm$^3$) | hexene (mL) | C$_2$ psi** | Activity | FI | Density g/cc |
|---|---|---|---|---|---|---|---|---|---|
| 1 | 0.0025 | 754 | 75 | 1000 | 200 | 120 | 34,793 | — | — |
| 2 | 0.009 | 336 | 75 | 2000 | 50 | 100 | 4,561 | — | 0.9554 |
| 3 | 0.004 | 1024 | 65 | 800 | 200 | 100 | 39,545 | 0.784 | 0.9465 |
| 4* | 0.004 | 1024 | 65 | 800 | 200 | 100 | 38,005 | 0.704 | 0.9368 |

*Run 4 involved activating the catalyst precursor with tris(pentafluorophenyl)boron for 10 minutes in toluene. All MAO was added to the reactor separately.
**100 psi = 0.69 MPa, 120 psi = 0.82 MPa Polymerization 2

A series of ethylene homopolymers was made in a laboratory scale, one liter autoclave reactor using the metal complex described in Example 3 with N,N-dimethylanilinium tetrakis(pentafluorophenyl)boron cocatalyst. In each case, the catalyst combination was prepared by combining a toluene solution of the catalyst precursor of Example 2 with one equivalent of cocatalyst yielding a bright orange solution and retaining the same for 10 minutes prior to injection into the reactor. Scavenging agents used included triisobutylaluminum (TBA), trimethylaluminum (TMA) and triethylaluminum (TEA). Reaction conditions and results are shown in Table 2 below. All polymerizations were conducted for 20 minutes, at an ethylene pressure of 100 psi (0.69 MPa), a reactor temperature of 65° C., in the absence of hydrogen or comonomer.

TABLE 2

| Run | mmol Zr | Scavenger (Al/Zr mole ratio) | Yield (g) | Activity (g/mmol-h-100 psi C$_2$)[1] |
|---|---|---|---|---|
| 5 | 0.004 | TMA (500) | 30.4 | 29,250 |
| 6 | 0.004 | TBA (497) | 4.5 | 4,330 |
| 7 | 0.004 | TEA (507) | 17.3 | 16,645 |

[1]equivalent to g/mmol-h-0.69 MPa C$_2$

What is claimed is:

1. A metal complex comprising a multidentate chelating ligand, said metal complexes corresponding to the formula:

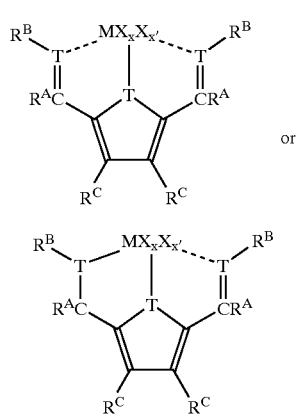

where M is a metal from one of Groups 3 to 13 of the Periodic Table of the Elements, the lanthanides or actinides;

T is nitrogen or phosphorus;

$R^A$ independently each occurrence is hydrogen, $R^B$ or $TR^B_j$, $R^B$ independently each occurrence is a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, and optionally the $R^B$ and $R^A$ groups bonded to the same T=C grouping may be joined together to form a divalent ligand group;

j is 1 or 2, and when j is 1, T' is oxygen or sulfur and when j is 2, T' is nitrogen or phosphorus, $R^C$ independently each occurrence is hydrogen or a group having from 1 to 80 atoms not counting hydrogen, which is hydrocarbyl, hydrocarbylsilyl, halo-substituted hydrocarbyl, hydrocarbyloxy-substituted hydrocarbyl, hydrocarbylamino-substituted hydrocarbyl, or hydrocarbylsilyl-substituted hydrocarbyl, or two $R^C$ groups are joined together forming a divalent ligand group;

X is an anionic ligand group having up to 60 atoms (excluding ligands that are cyclic, delocalized, π-bound ligand groups), and optionally two X groups together form a divalent ligand group;

X' independently each occurrence is a Lewis base ligand having up to 20 atoms;

x is a number from 0 to 5; and x' is zero, 1 or 2.

2. The complex of claim 1, wherein M is a metal of Groups 4–8;

T is nitrogen;

X is chloride or $C_{1-10}$ hydrocarbyl; and x' is zero.

3. The complex of claim 2 wherein independently each occurrence $R^A$ is hydrogen, methyl or phenyl, $R^B$ is aryl or alkyl substituted aryl, and $R^C$ is hydrogen.

4. The complex of claim 1 corresponding to the formula:

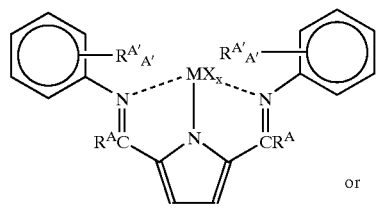

or

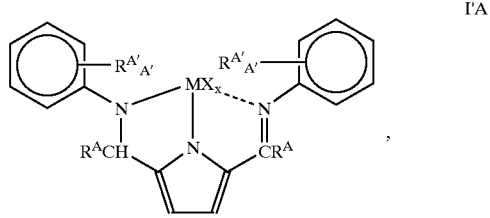

wherein $R^{A'}$ independently each occurrence is $C_{1-4}$ alkyl, most preferably methyl, isopropyl, or t-butyl, A' is 0, 1 or 2; $R^A$ is hydrogen, or $C_{1-10}$ hydrocarbyl, M is zirconium, vanadium or chromium; especially zirconium, X is halide or $C_{1-10}$ hydrocarbyl, and x is 1 or 2.

5. A metal complex according to claim 1 which is [(2-(2,6-diisopropylphenyl)-iminomethyl)-5-(2,6-diisopropylphenyl)amido(benzyl)methyl)pyrrol-1-yl]Zr dibenzyl.

6. A catalyst composition for olefin polymerization comprising:

(A) the metal complex of any one of claims 1–5; and (B) an activating cocatalyst wherein the molar ratio of (A) to (B) is from 1:10,000 to 100:1.

7. A process for polymerizing olefins comprising contacting one or more $C_{2-20}$ α-olefin under polymerization conditions with a catalyst composition according to claim 6.

8. A process for preparing isotactic polypropylene comprising contacting propylene under polymerization conditions with a catalyst composition according to claim 6.

* * * * *